United States Patent [19]

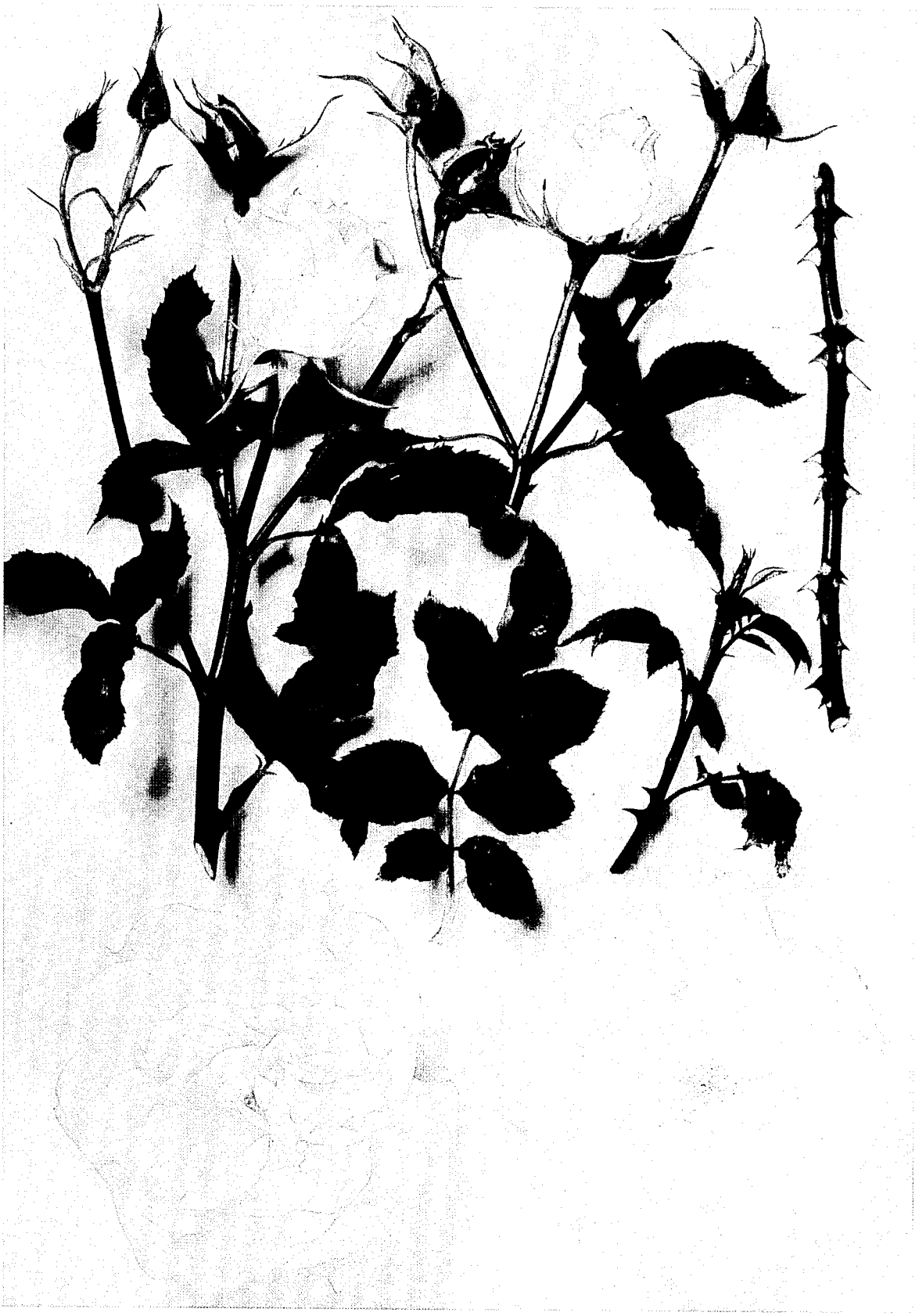

Warriner

[11] Plant 4,439

[45] Jul. 17, 1979

[54] ROSE PLANT

[75] Inventor: William A. Warriner, Tustin, Calif.

[73] Assignee: Jackson & Perkins Co., Medford, Oreg.

[21] Appl. No.: 890,866

[22] Filed: Mar. 27, 1978

[51] Int. Cl.[2] ..... A01H 5/00

[52] U.S. Cl. ..... Plt./17

[58] Field of Search ..... Plt./16-18

*Primary Examiner*—Robert E. Bagwill

*Attorney, Agent, or Firm*—Klarquist, Sparkman, Campbell, Leigh, Hall & Whinston

[57] ABSTRACT

A vigorous upright rose plant of the hybrid tea class that blooms in clusters of several blooms during Spring and early Summer, its bud and bloom color being Chinese Coral and having a very light fragrance.

5 Drawing Figures

BACKGROUND OF THE INVENTION

The present invention relates to a new and distinct variety of rose plant of the hybrid tea class which was originated by me by crossing the variety Bridal Pink, U.S. Plant Pat. No. 2,851 with pollen of the variety Polynesian Sunset, U.S. Plant Pat. No. 2,530.

The primary objective of this breeding was to produce a new rose variety of the hybrid tea class, but with blooms also borne in attractive clusters of large flowers, in a color range between the two parent varieties. This objective was substantially achieved along with other desirable improvements as evidenced by the following unique combination of characteristics which are obvious in the new variety and which distinguish it from its parents and from all other varieties of which I am aware:

1. A vigorous, upright plant of the hybrid tea type.
2. Main canes and side branches terminating in clusters of several blooms during Spring and early Summer growth.
3. Bud and flower color near Wilson's Chinese Coral.
4. Very little fragrance.

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with Wilson's Horticultural Color Chart, except where ordinary dictionary significance of color is indicated.

Parentage:

*Seed parent.*—Bridal Pink, U.S. Plant Pat. No. 2,851.

*Pollen parent.*—Polynesian Sunset, U.S. Plant Pat. No. 2,530.

Classification:

*Botanical.*—Rosa hybrid.

*Commercial.*—Hybrid Tea.

FLOWER

Observations made from specimens grown in the greenhouse and in the garden at Irvine, Calif., in early December, 1977.

Blooming Habit: Continuous.

Bud:

*Size.*—1.25 inches when petals start to unfurl.

*Form.*—Long, pointed ovoid.

*Color.*—When sepals first divide Upper side Mars Orange (013) quickly fading to Mars Orange (013/2). Reverse side - near Chinese Coral (614/2). When half blown; upper side of petals near Chinese Coral (614/1); lower side of petals near Chinese Coral (614/1).

*Sepals.*—Color: Outer surface Scheeles Green (860) overlaid in the midportion with Garnette Brown (00918/3); Inner surface Scheeles Green (860/3) with moderate amount of white tomentum. Three appendaged sepals, normally appendaged. Two unappendaged sepals, hairy edged.

*Receptacle.*—Color: Scheeles Green (860) often overlaid with Garnette Brown (00918/3). Shape: Funnel. Size: Large. Surface: Smooth.

*Peduncle.*—Length: Medium. Surface: Slightly prickly. Color: Medium green and bronzy. Strength: Bending, slender.

*Opening.*—Outer petals roll back spirally.

Bloom:

*Size.*—Large. Average open size 4 to five inches.

*Borne.*—Singly and in clusters. If in clusters, irregular.

*Stems.*—Long.

*Form.*—When first open, high centered. Permanence — flattens when fully opened.

*Petalage.*—Number of petals under normal conditions — 35.

*Color.*—Center of flower: Upper side of petals Chinese Coral (614/1). Reverse side of petals Chinese Coral (614/1). Base of petals - a large area of Lemon yellow (4/2) on both upper and lower surface of petals. General tonality from a distance Chinese Coral (614/1).

*Variegations.*—None.

*Discoloration.*—None. At end of third day Chinese Coral (614/1).

*Fragrance.*—Slight.

Petals:

*Texture.*—Thick.

*Shape.*—Round. urved

*Form.*—Tips slightly recurved and edges slightly quilled.

*Arrangement.*—Informal. Imbricated. Petaloids in center, few.

*Persistence.*—Drop off cleanly.

*Lastingness.*—On the plant — long. As cut flower — long.

Reproductive parts:

*Stamens, anthers.*—Medium. Color — yellow. Arrangement — regular around styles.

*Filaments.*—Color: yellow.

*Pollen.*—Lemon yellow. r — Rose

*Styles.*—Color—Rose Red (724).

*Stigmas.*—Color — White.

PLANT

Form: Bush.

Growth: Very vigorous, upright, branching. Often blooms in clusters, especially on Spring growth, but retains the tall, upright habit generally associated with the hybrid tea class.

Foliage: Number of leaflets on normal mid-stem leaves: 5 or 7.

*Size.*—Large.

*Quantity.*—Normal.

*Color.*—New foliage: slightly lighter than Garnette Brown (00918/3). Old foliage: near Spinach Green (0960).

Leaflets:

*Shape.*—Oval pointed.

*Texture.*—Leathery.

*Edge.*—Serrated, undulated.

*Serration.*—Single, small.

*Petiole.*—Rachis: Color, green. Underside: prickly.

*Stipules.*—Medium, smooth.

*Disease resistance.*—Normally resistant to mildew under normal growing conditions at Irvine, Calif.

Wood:

*New wood.*—Color: reddish. Bark: smooth.

*Old wood.*—Color: green. Bark: smooth.

Prickles:

*Quantity.*—On main stalks from base, ordinary. On laterals from stalk, ordinary.

*Form.*—Long base, long, hooked downward.

*Color when young.*—Red.

*Position.*—Irregular.

Small Prickles:

*Quantity.*—On main stalks — none. On laterals — none.

I claim:

1. A new and distinct variety of rose plant of the hybrid tea class, substantially as herein shown and described, characterized particularly as to novelty by the unique combination of its vigorous, upright habit of growth; its tendency to bloom in clusters of several blooms during Spring and early Summer; its bud and flower color of Wilson's Chinese Coral; its very light fragrance.

* * * * *

UNITED STATES PATENT AND TRADEMARK OFFICE

CERTIFICATE OF CORRECTION

PATENT NO. : Plant 4439

DATED : July 17, 1979

INVENTOR(S) : William A. Warriner

It is certified that error appears in the above-identified patent and that said Letters Patent are hereby corrected as shown below:

Column 2, line 48, "(614/1)" should be --(614/2)--.

Signed and Sealed this

*Eighth* Day of *January 1980*

[SEAL]

*Attest:*

SIDNEY A. DIAMOND

*Attesting Officer*

*Commissioner of Patents and Trademarks*